United States Patent
Hilmersson

(10) Patent No.: US 10,314,541 B2
(45) Date of Patent: Jun. 11, 2019

(54) SENSOR GUIDE WIRE

(75) Inventor: Mats Hilmersson, Bromma (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 940 days.

(21) Appl. No.: 13/823,063

(22) PCT Filed: Sep. 28, 2011

(86) PCT No.: PCT/EP2011/066864
§ 371 (c)(1),
(2), (4) Date: Mar. 13, 2013

(87) PCT Pub. No.: WO2012/041905
PCT Pub. Date: Apr. 5, 2012

(65) Prior Publication Data
US 2013/0172782 A1    Jul. 4, 2013

Related U.S. Application Data

(60) Provisional application No. 61/387,695, filed on Sep. 29, 2010.

(30) Foreign Application Priority Data
Sep. 29, 2010 (SE) ...................................... 1051005

(51) Int. Cl.
*A61B 5/00* (2006.01)
*A61B 5/0215* (2006.01)
(Continued)

(52) U.S. Cl.
CPC .............. *A61B 5/6851* (2013.01); *A61B 5/01* (2013.01); *A61B 5/0215* (2013.01); *A61B 5/036* (2013.01);
(Continued)

(58) Field of Classification Search
CPC ....................................................... A61B 5/00
(Continued)

(56) References Cited

U.S. PATENT DOCUMENTS

RE35,648 E      11/1997  Tenerz et al.
5,707,354 A *   1/1998   Salmon ................... A61F 2/958
                                                    600/585
(Continued)

FOREIGN PATENT DOCUMENTS

EP    1 475 036 B1    11/2004
EP    1 479 407 B1    11/2004
(Continued)

OTHER PUBLICATIONS

Japanese Office Action and English language translation dated Dec. 2, 2014, 7 pgs.
(Continued)

*Primary Examiner* — May A Abouelela
(74) *Attorney, Agent, or Firm* — Foley & Lardner LLP

(57) ABSTRACT

The present invention relates to a sensor guide wire (1) for intravascular measurements of at least one variable in a living body, which sensor guide wire (1) has a proximal region (2), a distal sensor region (3) and a tip region (4). The sensor guide wire (1) comprises, a sensor element arranged in said sensor region (3), a tip region core wire (5) having a longitudinal axis (6) and extending essentially along said tip region (4), and a coil (7) arranged in said tip region (4). The coil (7) at least partly encloses said tip region core wire (5), and a distal tip joint (8) is arranged at a distal end (9) of said sensor guide wire (1) for attaching said coil (7) to said tip region core wire (5). A major part of said tip region core wire (5) has a circular cross-section in a plane perpendicular to said longitudinal axis (6).

34 Claims, 2 Drawing Sheets

(51) Int. Cl.
  *A61B 5/01* (2006.01)
  *A61B 5/03* (2006.01)
  *A61B 5/05* (2006.01)
  *A61M 25/09* (2006.01)
(52) U.S. Cl.
  CPC ..... *A61B 5/05* (2013.01); *A61M 2025/09083* (2013.01); *A61M 2025/09175* (2013.01)
(58) Field of Classification Search
  USPC ........................................................ 600/585
  See application file for complete search history.

(56) References Cited

U.S. PATENT DOCUMENTS

| | | | |
|---|---|---|---|
| 5,730,717 A * | 3/1998 | Gelbfish | A61B 17/22 600/566 |
| 5,836,893 A | 11/1998 | Urick | |
| 5,951,480 A * | 9/1999 | White | A61B 8/12 600/463 |
| 5,957,865 A | 9/1999 | Backman et al. | |
| 6,167,763 B1 | 1/2001 | Tenerz et al. | |
| 6,190,332 B1 | 2/2001 | Muni et al. | |
| RE37,148 E | 4/2001 | Shank | |
| 6,261,246 B1 * | 7/2001 | Pantages | A61B 8/12 600/459 |
| 6,290,656 B1 | 9/2001 | Boyle et al. | |
| 6,352,515 B1 | 3/2002 | Anderson et al. | |
| 6,464,699 B1 | 10/2002 | Swanson | |
| 6,464,700 B1 | 10/2002 | Koblish et al. | |
| 6,692,491 B1 | 2/2004 | Phan | |
| 6,866,642 B2 | 3/2005 | Kellerman et al. | |
| 7,052,473 B2 * | 5/2006 | Hill | A61M 25/0138 128/899 |
| 7,115,101 B2 | 10/2006 | Cornelius et al. | |
| 7,169,118 B2 | 1/2007 | Reynolds et al. | |
| 7,175,619 B2 | 2/2007 | Koblish et al. | |
| 7,214,201 B2 | 5/2007 | Burmeister et al. | |
| 7,399,283 B2 | 7/2008 | Kato | |
| 7,455,646 B2 | 11/2008 | Richardson et al. | |
| 7,724,148 B2 | 5/2010 | Samuelsson et al. | |
| 7,789,839 B2 | 9/2010 | Lupton | |
| 7,942,832 B2 | 5/2011 | Kanuka et al. | |
| 8,075,497 B2 | 12/2011 | Melsheimer | |
| 8,105,246 B2 | 1/2012 | Voeller et al. | |
| 8,133,190 B2 | 3/2012 | Melsheimer et al. | |
| 8,174,395 B2 | 5/2012 | Samuelsson et al. | |
| 8,222,566 B2 | 7/2012 | Shireman et al. | |
| 8,257,278 B2 | 9/2012 | Howland et al. | |
| 8,277,386 B2 | 10/2012 | Ahmed et al. | |
| 8,360,995 B2 | 1/2013 | Elsesser et al. | |
| 8,419,658 B2 | 4/2013 | Eskuri | |
| 8,460,213 B2 | 6/2013 | Northrop | |
| 8,461,997 B2 | 6/2013 | Samuelsson et al. | |
| 8,602,974 B2 * | 12/2013 | Goldwasser | A61B 1/01 600/115 |
| 8,608,670 B2 | 12/2013 | Matsumoto et al. | |
| 8,608,703 B2 | 12/2013 | Riles et al. | |
| 8,698,638 B2 | 4/2014 | Samuelsson et al. | |
| 8,758,269 B2 | 6/2014 | Miyata et al. | |
| 8,784,337 B2 | 7/2014 | Voeller et al. | |
| 8,845,551 B2 | 9/2014 | Kato | |
| 9,028,427 B2 | 5/2015 | Kinoshita et al. | |
| 9,095,685 B2 | 8/2015 | Sela et al. | |
| 9,155,492 B2 | 10/2015 | Jenkins et al. | |
| 2002/0032390 A1 | 3/2002 | Jafari | |
| 2002/0188189 A1 * | 12/2002 | Belef | A61B 8/12 600/407 |
| 2004/0167436 A1 * | 8/2004 | Reynolds | A61M 25/09 600/585 |
| 2004/0167438 A1 | 8/2004 | Sharrow | |
| 2004/0193034 A1 * | 9/2004 | Wasicek | A61M 25/0169 600/407 |
| 2006/0074318 A1 * | 4/2006 | Ahmed | A61B 5/02158 600/465 |
| 2006/0116571 A1 * | 6/2006 | Maschke | A61B 5/0066 600/424 |
| 2006/0247672 A1 | 11/2006 | Vidlund et al. | |
| 2007/0167972 A1 | 7/2007 | Euteneuer et al. | |
| 2007/0244413 A1 | 10/2007 | Biggins | |
| 2007/0255145 A1 * | 11/2007 | Smith | A61B 5/0215 600/485 |
| 2008/0119762 A1 | 5/2008 | Tateishi et al. | |
| 2008/0306468 A1 | 12/2008 | Tamai et al. | |
| 2009/0062602 A1 * | 3/2009 | Rosenberg | A61M 25/0147 600/101 |
| 2009/0088650 A1 | 4/2009 | Corl | |
| 2009/0198153 A1 * | 8/2009 | Shriver | A61B 17/00234 600/585 |
| 2009/0254000 A1 | 10/2009 | Layman et al. | |
| 2010/0030113 A1 * | 2/2010 | Morriss | A61B 1/233 600/585 |
| 2010/0222637 A1 * | 9/2010 | Kassab | A61B 5/02152 600/17 |
| 2010/0228112 A1 | 9/2010 | Von Malmborg | |
| 2011/0098648 A1 | 4/2011 | Kato | |
| 2011/0213220 A1 | 9/2011 | Samuelsson et al. | |
| 2012/0041342 A1 | 2/2012 | Purtzer | |
| 2012/0289808 A1 | 11/2012 | Hubinette | |
| 2013/0237864 A1 | 9/2013 | Mazar et al. | |
| 2014/0005543 A1 | 1/2014 | Burkett | |
| 2014/0066790 A1 | 3/2014 | Burkett et al. | |
| 2014/0066791 A1 | 3/2014 | Burkett | |
| 2014/0180141 A1 | 6/2014 | Millett | |
| 2014/0180166 A1 | 6/2014 | Isch | |
| 2014/0187978 A1 | 7/2014 | Millett et al. | |
| 2014/0187979 A1 | 7/2014 | Burkett | |
| 2015/0094616 A1 | 4/2015 | Simpson et al. | |
| 2016/0022215 A1 | 1/2016 | Henderson et al. | |

FOREIGN PATENT DOCUMENTS

| | | |
|---|---|---|
| EP | 1 267 737 B1 | 10/2005 |
| EP | 1 616 521 A1 | 1/2006 |
| JP | 2002-538854 A | 11/2002 |
| JP | 2006-026406 A | 2/2006 |
| JP | 2006-519062 A | 8/2006 |
| JP | 3876080 B2 | 1/2007 |
| JP | 2010-187929 A | 2/2010 |
| JP | 5229830 B2 | 7/2013 |
| JP | 2014-023943 A | 2/2014 |
| JP | 5751624 B2 | 7/2015 |
| WO | WO 00/38775 A2 | 7/2000 |
| WO | WO 2004/075950 A2 | 9/2004 |
| WO | WO 2009/054800 A1 | 4/2009 |

OTHER PUBLICATIONS

Japanese Office Action and English translation, dated Aug. 30, 2016, 14 pages.
Japanese Office Action and English translation, dated Feb. 7, 2017, 8 pages.
Japanese Office Action and English language translation dated Oct. 31, 2017, 9 pages.
USPTO Office Action, U.S. Appl. No. 15/072,021, dated Apr. 2, 2018, 8 pages.
USPTO Office Action, U.S. Appl. No. 15/072,021, dated Sep. 14, 2018, 17 pages.
International Preliminary Report on Patentability, PCT/US2017/022514, dated Sep. 27, 2018, 7 pages.
Japanese Office Action and English translation, Application No. 2018-054871, dated Feb. 26, 2019, 8 pages.
USPTO Office Action, U.S. Appl. No. 15/072,021, dated Feb. 25, 2019, 18 pages.

* cited by examiner

SENSOR GUIDE WIRE

FIELD OF THE INVENTION

The present invention relates to a sensor guide wire, and in particular a special design of a sensor guide wire tip according to the preamble of the independent claim.

BACKGROUND OF THE INVENTION

In many medical procedures, various physiological conditions present within a body cavity need to be monitored. These physiological conditions are typically physical in nature—such as pressure, temperature, rate-of-fluid flow, and provide the physician or medical technician with critical information as to the status of a patient's condition.

One device that is widely used to monitor conditions is the blood pressure sensor. A blood pressure sensor senses the magnitude of a patient's blood pressure, and converts it into a representative electrical signal that is transmitted to the exterior of the patient.

For most applications it is required that the sensor is electrically energized. Some means of signal and energy transmission is thus required, and most commonly extremely thin electrical cables, sometimes called microcables, are provided inside a guide wire, which itself is provided in the form of a tube, which often has an outer diameter in the order of 0.35 mm, and oftentimes is made of steel.

In order to increase the bending strength of the tubular guide wire, a core wire is positioned inside the tube. The core wire also helps to improve "pushability" and "torquability" of the guide wire. The mentioned electrical cables are e.g. positioned in the space between the inner lumen wall and the core wire.

Sensor and guide wire assemblies in which a sensor is mounted at the distal end of a guide wire are known. In U.S. Pat. Re. 35,648, which is assigned to the present assignee, an example of such a sensor and guide wire assembly is disclosed, where a sensor guide comprises a sensor element, an electronic unit, a signal transmitting cable connecting the sensor element to the electronic unit, a flexible tube having the cable and the sensor element disposed therein, a solid metal wire, and a coil attached to the distal end of the solid wire. The sensor element comprises a pressure sensitive device, typically a membrane, with piezoresistive elements connected in a Wheatstone bridge-type of arrangement mounted thereon.

As is disclosed in, for example, U.S. Pat. No. 6,167,763, which also is assigned to the present assignee, the sensor element can be arranged inside a short tube (usually referred to as a sleeve or jacket), which protects the sensor element and comprises an aperture through which the pressure sensitive device is in contact with the ambient medium. The U.S. Pat. No. 6,167,763 further illustrates that a first coil may be attached to the distal end of the jacket and that a similar second coil may be attached to the proximal end of the jacket. The solid metal wire—which, as also mentioned above, in the art usually is referred to as the core wire—extends through the interior of the jacket and may be provided with an enlarged diameter portion adapted for mounting of the sensor element.

In WO 2009/054800 A1, assigned to the present assignee, another example of a sensor guide wire for intravascular measurements of physiological variables in a living body, is disclosed. The sensor guide wire has a proximal shaft region, a flexible region and a distal sensor region. In one embodiment sensor guide wire is provided with a tip wire comprising a tip core wire.

It is advantageous if the sensor guide wire tip is flexible in order to make the various bends and turns that are necessary to navigate through the tortuous vessels, e.g. when navigating the sensor guide wire through coronary arteries. In sensor guide wires according to the Prior Art, as disclosed in for example the above mentioned U.S. Pat. Re. 35,648, the distal tip portion of the sensor guide wire is often made more flexible by grinding the core wire to a smaller dimension. Oftentimes, as also disclosed in U.S. Pat. Re. 35,648, the core wire is flattened in order to make the tip more flexible. A flattened core wire tip is mainly flexible in two directions.

This is also illustrated by e.g. US 2007/0255145, which discloses a sensor guide wire, provided with a core wire which is flattened at the tip of the sensor guide wire.

Besides from being flexible enough, it is also important that the sensor guide wire tip responds when steering the sensor guide wire through the tortuous vessels, i.e. the sensor guide wire tip must also have sufficient "steering response". "Steering response" is a measure of the irregular behavior of a sensor guide wire when the sensor guide wire tip is subjected to a non-linear pathway and rotated. The "steering response" of a sensor guide wire tip is a general property of the distal tip components.

The present inventors have identified some situations when applying the sensor guide wire in tortuous vessels where improved properties regarding flexibility, pull strength and steering response of the sensor guide wire tip would be advantageous.

An object of the present invention is therefore to provide an improved sensor guide wire comprising an improved tip, with sufficient pull strength and which tip is flexible in all directions, and which also is improved regarding the capability of being steered through the various bends and turns in the vessels.

SUMMARY OF THE INVENTION

The above-mentioned objects are achieved by the present invention according to the independent claim.

Preferred embodiments are set forth in the dependent claims.

Thus, according to the present invention a sensor guide wire is provided, which is less expensive to manufacture, and for which flexibility is improved, and which at the same time has sufficient pull strength and steering response.

These objects are achieved by a sensor guide wire provided with a core wire having a circular cross-section in a major part of the tip region.

The sensor guide wire for intravascular measurements of at least one variable in a living body, in accordance with the present invention, has a proximal region, a distal sensor region and a tip region. The sensor guide wire comprises, a sensor element arranged in the sensor region, a tip region core wire having a longitudinal axis and extending essentially along the tip region, and a coil arranged in the tip region. The coil at least partly encloses the tip region core wire, wherein a distal tip joint is arranged at a distal end of the sensor guide wire for attaching the coil to the tip region core wire. According to the present invention a major part of the tip region core wire has a circular cross-section in a plane perpendicular to the longitudinal axis.

The tip region core wire of the present invention provides a desired combination of flexibility and pull strength of the tip region core wire. The present invention further provides a sensor guide wire having a tip region with a desired steering response.

SHORT DESCRIPTION OF THE APPENDED DRAWINGS

DETAILED DESCRIPTION OF PREFERRED EMBODIMENTS OF THE INVENTION

Throughout the application the word distal refers to the part located furthest away in respect of the operator, and the word proximal refers to the part located closest in respect of the operator.

Figure 1:
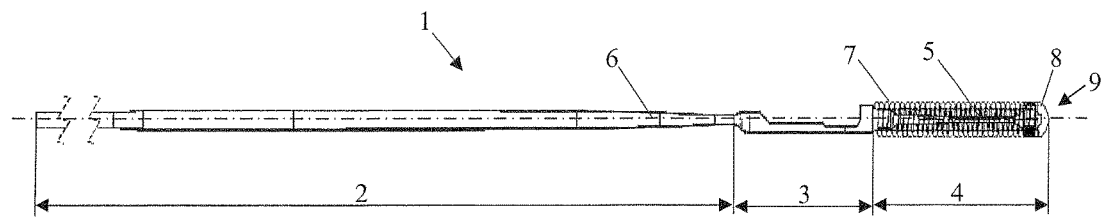
FIG. 1 shows the sensor guide wire according to the present invention.

FIG. 1 illustrates a sensor guide wire 1 for intravascular measurements of at least one variable in a living body, which sensor guide wire 1 has a proximal region 2, a distal sensor region 3 and a tip region 4. The sensor guide wire 1 comprises a sensor element (not shown) arranged in the sensor region 3, a tip region core wire 5 having a longitudinal axis 6 and extending essentially along the tip region 4, and a coil 7 arranged in the tip region 4. The coil 7 at least partly encloses the tip region core wire 5, wherein a distal tip joint 8 is arranged at a distal end 9 of the sensor guide wire 1 for attaching the coil 7 to the tip region core wire 5.

Figure 2A:
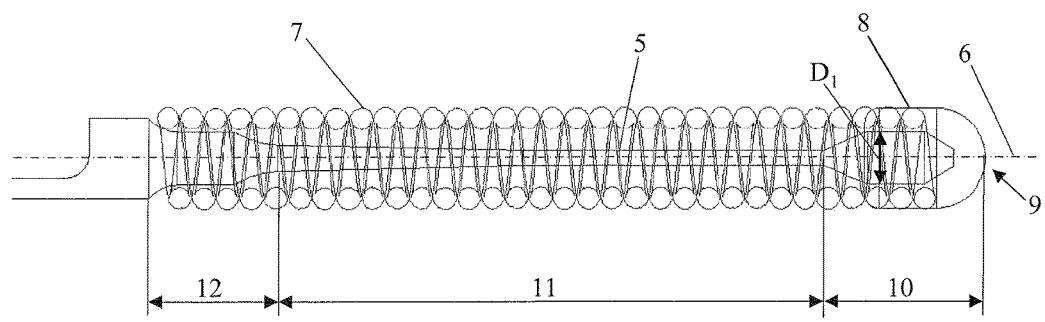
FIG. 2a shows the tip region of the sensor guide wire according to one embodiment of the present invention, wherein the tip region core wire is tapering distally in the tip portion.
Figure 2B:
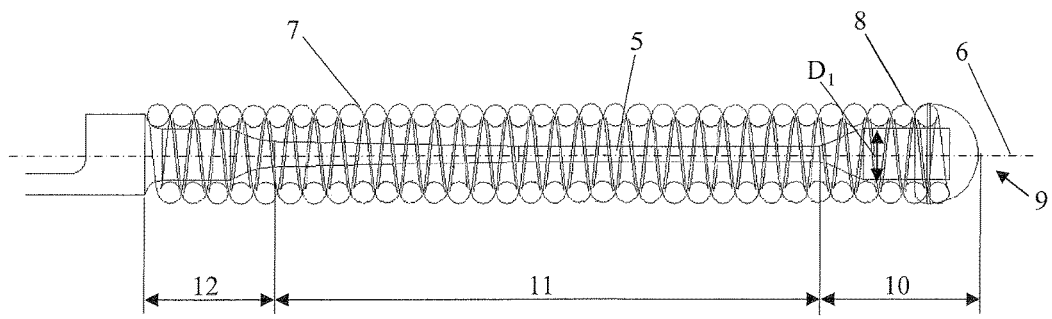
FIG. 2b shows the tip region of the sensor guide wire according to one embodiment of the present invention, wherein the tip region core wire has a uniform diameter distally in the tip portion.

FIGS. 2a and 2b illustrates the tip region 4 of the sensor guide wire 1, according to the present invention. A major part of the tip region core wire 5 has a circular cross-section in a plane perpendicular to the longitudinal axis 6. The circular cross-section of the tip region core wire 5 makes the sensor guide wire 1 flexible in all directions in the tip region 4 and hence, an improved flexibility of the sensor guide wire 1 is achieved. The circular cross-section also provides for sufficient pull strength of the tip region core wire 5.

According to the present invention, the measured variable may be a physiological variable, such as e.g. pressure, flow, or temperature, or another variable, such as e.g. externally generated radio waves, or magnetic waves.

According to one embodiment of the present invention, the tip region core wire 5 has a circular cross-section in a plane perpendicular to the longitudinal axis 6 in the entire tip region 4.

According to another embodiment of the present invention, the major part of the tip region core wire 5, having a circular cross-section in a plane perpendicular to the longitudinal axis 6, is at least 75% of the entire length of the tip region core wire 5.

As further illustrated in FIGS. 2a and 2b, the tip region 4 only consists of the tip region core wire 5, the coil 7 and the distal tip joint 8. The tip region core wire 5 provides a sensor guide wire tip having an advantageous combination of pull strength and flexibility in the tip region 4 such that there is no need for any further reinforcements of the sensor guide wire 1 in the tip region 4. The length of the tip region 4 is preferably between 25 mm and 35 mm, more preferably between 28 mm and 32 mm.

FIGS. 2a and 2b further shows that the tip region core wire 5 comprises a distal portion 10, an intermediate portion 11, and a proximal portion 12. The distal portion 10 of the tip region core wire 5 is the portion closest to the distal end 9 of the sensor guide wire 1, and the proximal portion 12 is the portion closest to the sensor region 3. Further, the distal portion 10 has a circular cross-section in a plane perpendicular to the longitudinal axis 6. The length of the distal portion 10 is preferably between 0 and 5 mm, more preferably between 0.6 and 1.6 mm.

In one embodiment, as illustrated in FIG. 2a, the distal portion 10 of the tip region core wire 5 has a circular cross-section and is distally tapering along the longitudinal axis 6 towards the distal end 9. According to another embodiment, as shown in FIG. 2b, the diameter $D_1$ of the distal tip portion 10 of the tip region core wire 5 is uniform along the longitudinal axis 6 closest to the distal end 9.

In one embodiment, and order to fasten the coil 7 to the distal portion 10, the inner diameter of the coil 7 is adapted to an outer diameter $D_1$ of the distal portion 10. The outer diameter $D_1$ of the circular cross-section of the distal portion 10 is preferably between 0.10 and 0.25 mm, more preferably between 0.17 and 0.20 mm.

According to one embodiment, the intermediate portion 11 has a circular cross-section in a plane perpendicular to the longitudinal axis 6. The distal portion 10 may have a larger cross-sectional diameter $D_1$ than the cross-sectional diameter $D_2$ of the intermediate portion 11. The diameter $D_2$ of the circular cross-section of the intermediate portion 10 may be between 0.035 mm and 0.187 mm, more preferably between 0.048 mm and 0.157 mm.

In one embodiment the tip region core wire 5 is made from steel and the cross-sectional diameter $D_2$ of the intermediate portion 11 is between 0.065 mm and 0.035 mm.

According to yet another embodiment, the tip region core wire 5 is made from nitinol and the cross-sectional diameter $D_2$ of the intermediate portion 11 is between 0.085 mm and 0.055 mm.

Figure 3:
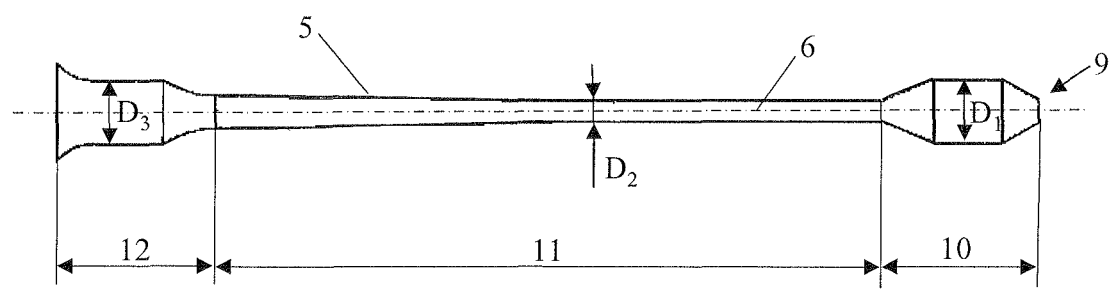
FIG. 3 shows the tip region core wire according to the present invention, where the coil and the distal tip joint is omitted for sake of simplicity.

Furthermore, the diameter $D_2$ may vary along the longitudinal axis 6 in the intermediate portion 11. In one preferred embodiment, as illustrated in FIG. 3, the intermediate portion 11 is tapering towards the distal portion 10. In a further preferred embodiment, the proximal half of the intermediate portion 11 is tapered, and the distal half is cylindrical. However, as obvious constructional variations, the intermediate portion 11 may instead have equal or larger cross-sectional diameter $D_2$ than the outer diameter $D_1$ of the distal portion 10, or the intermediate portion 11 may be tapering towards the proximal portion 12.

In FIG. 3 it is further shown that, the distal portion 10 distally is tapering along the longitudinal axis 6 towards the distal end 9. Furthermore, the distal portion 10 proximally is tapering along the longitudinal axis towards the intermediate portion 11, and the intermediate portion 11 in its turn is tapering distally along the longitudinal axis 6 towards the distal portion 10.

FIGS. 2-3 also shows that the proximal portion 12 has a circular cross-section in a plane perpendicular to the longitudinal axis 6. The outer diameter $D_3$ of the circular cross-section of the proximal portion 12 is preferably between 0.10 and 0.25 mm, more preferably between 0.17 and 0.20 mm. According to the embodiment shown in FIGS. 2-3, the outer diameter $D_3$ of the proximal portion 12 is larger proximally than distally. Furthermore, the proximal portion 12 is tapering along the longitudinal axis 6 in a distal direction. The length of proximal portion 12 is preferably between 0.1 mm and 0.6 mm, more preferably between 0.2 mm and 0.4 mm.

Figure 4:
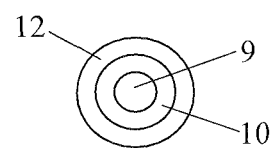
FIG. 4 shows a front view of the tip region core wire shown in FIG. 3 according to the present invention.

FIG. 4 illustrates a front view of the tip region core wire 5 shown in FIG. 3. The distal portion 10 has a circular cross-section and is distally tapering along the longitudinal axis 6 towards the distal end 9. FIG. 4 also shows that the proximal portion 12 has an equivalent cross-sectional diameter compared to the distal portion 10 according to this preferred embodiment.

According to one embodiment the sensor element is arranged in a hollow jacket (not shown), which jacket has a circular cross section in a plane perpendicular to the longitudinal axis 6. An inner diameter of the tubular jacket may then be adapted to the outer diameter $D_3$ of the proximal portion 12.

According to the present invention, the distal tip joint 8 attaches the coil 7 to the tip region core wire 5. The distal tip joint 8 is preferably soldered or welded. However, other suitable techniques may alternatively be used in order to fasten the coil 7 to the tip region core wire 5. The combination of that the inner diameter of the coil 7 is adapted to an outer diameter $D_1$ of the distal portion 10, and the distal tip joint 8, improves the structural integrity of the sensor guide wire 1.

As discussed in the background section a sensor guide wire is advantageously provided with a core wire running along essentially the entire length of the sensor guide wire. This is also applied in the sensor guide wire according to the present invention, with the difference that the distal part of the core wire, i.e. in the tip region 4, being the tip region core wire 5 as described herein.

In one embodiment the tip region core wire is unitary with the remaining main core wire.

In another embodiment the tip region core wire is separate from the main core wire. In this embodiment the proximal part of the tip region core wire 5 is preferably attached to e.g. a jacket.

As also mentioned above, the tip region core wire 5 is preferably made from nitinol or steel, although other similar materials having suitable material properties may be used.

The sensor guide wire 1 may further comprise at least one microcable extending at least partly along the sensor guide wire 1 and being connected to the sensor element.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A sensor guide wire for intravascular measurement of at least one variable in a living body, the sensor guide wire having a proximal region, a sensor region located distal of the proximal region, and a tip region located distal of the sensor region, comprising:
   a sensor element located in said sensor region;
   a core wire having a longitudinal axis and extending along the proximal region, the sensor region, and the tip region, wherein the core wire includes a tip region core wire part having a longitudinal axis and extending along the tip region; and
   a coil located in the tip region, the coil at least partly enclosing the tip region core wire part;
   wherein the tip region core wire part comprises a proximal portion, an intermediate portion, and a distal portion, disposed in order in a distal direction,
   wherein the proximal portion of the tip region core wire part includes a constant cross-sectional thickness region and a tapered cross-sectional thickness region,
   wherein a cross-sectional thickness of the core wire at a distal end of the sensor region is larger than a cross-sectional thickness of the core wire at the constant cross-sectional thickness region of the proximal portion of the tip region core wire part,
   wherein a cross-sectional thickness of the core wire at the distal portion of the tip region core wire part is larger than a cross-sectional thickness of the core wire at the intermediate portion of the tip region core wire part,
   wherein the intermediate portion of the tip region core wire part includes a proximal region and a distal region,
   wherein an entirety of the proximal region of the intermediate portion is tapered so as to have a cross-sectional thickness that decreases in the distal direction, and
   wherein the distal region of the intermediate portion is at least as long as the proximal region of the intermediate portion,
   wherein a length of the proximal region of the intermediate portion is greater than a length of the proximal portion of the tip region core wire part,
   wherein a length of the distal region of the intermediate portion is greater than a length of the proximal portion of the tip region core wire part, and
   wherein a distal end of the coil is attached to an outer surface of the distal portion of the tip region core wire part by a distal tip joint, thereby attaching the coil to the tip region core wire part,
   wherein the sensor region of the core wire comprises an upward-facing sensor element mounting surface, and
   wherein each of the cross-sectional thicknesses is defined in an upward-downward direction.

2. The sensor guide wire according to claim 1, wherein an inner diameter of the coil is adapted to an outer thickness of the distal portion.

3. The sensor guide wire according to claim 1, wherein an outer cross-sectional thickness of the intermediate portion is between 0.035 mm and 0.187 mm.

4. The sensor guide wire according to claim 1, wherein an outer cross-sectional thickness of the intermediate portion is between 0.048 mm and 0.157 mm.

5. The sensor guide wire according to claim 1, wherein an outer cross-sectional thickness of the distal portion is between 0.10 mm and 0.25 mm.

6. The sensor guide wire according to claim 1, wherein an outer cross-sectional thickness of the distal portion is between 0.17 mm and 0.20 mm.

7. The sensor guide wire according to claim 1, wherein an outer cross-sectional thickness of the intermediate portion is between 0.035 mm and 0.187 mm and an outer cross-sectional thickness of the distal portion is between 0.10 mm and 0.25 mm.

8. The sensor guide wire according to claim 1, wherein an entirety of the tip region core wire part has a circular cross-section.

9. The sensor guide wire according to claim 1, wherein a length of the tip region is between 25 mm and 35 mm.

10. The sensor guide wire according to claim 1, wherein a length of the tip region is between 28 mm and 32 mm.

11. The sensor guide wire according to claim 1, wherein a length of the distal portion is between 0 and 5 mm.

12. The sensor guide wire according to claim 1, wherein a length of the distal portion is between 0.6 and 1.6 mm.

13. The sensor guide wire according to claim 1, wherein at least 75% of an overall length of the tip region core wire part has a circular cross-section.

14. The sensor guide wire according to claim 1, wherein the distal portion has a circular cross-section in a plane perpendicular to the longitudinal axis.

15. The sensor guide wire according to claim 1, wherein the distal portion is tapered along the longitudinal axis towards the distal end.

16. The sensor guide wire according to claim 1, wherein the distal portion is tapered along the longitudinal axis towards the intermediate portion.

17. The sensor guide wire according to claim 1, wherein the proximal portion of the tip region core wire part has a circular cross-section in a plane perpendicular to the longitudinal axis.

18. The sensor guide wire according to claim 17, wherein an outer cross-sectional thickness of the proximal portion is between 0.10 mm and 0.25 mm.

19. The sensor guide wire according to claim 17, wherein an outer cross-sectional thickness of the proximal portion is between 0.17 mm and 0.20 mm.

20. The sensor guide wire according to claim 17, wherein an outer cross-sectional thickness of the proximal portion is larger proximally than distally.

21. The sensor guide wire according to claim 17, wherein the proximal portion is tapered along the longitudinal axis in a distal direction.

22. The sensor guide wire according to claim 1, wherein the sensor element is arranged in a hollow jacket.

23. The sensor guide wire according to claim 22, wherein the jacket has a circular cross-section in a plane perpendicular to the longitudinal axis.

24. The sensor guide wire according to claim 22, wherein an inner diameter of the jacket is adapted to an outer cross-sectional thickness of the proximal portion of the tip region core wire part.

25. The sensor guide wire according to claim 1, wherein the intermediate portion has a circular cross-section in a plane perpendicular to the longitudinal axis.

26. The sensor guide wire according to claim 1, wherein the distal end of the coil is soldered or welded to the outer surface of the distal portion of the tip region core wire part.

27. The sensor guide wire according to claim 1, wherein the tip region core wire part is made from nitinol or steel.

28. The sensor guide wire according to claim 1, further comprising at least one microcable extending at least partly along the sensor guide wire and being connected to the sensor element.

29. The sensor guide wire according to claim 1, wherein (i) an outer cross-sectional thickness of a distal end of the intermediate portion of the tip region core wire part is smaller than (ii) an outer cross-sectional thickness of a proximal end of the intermediate portion of the tip region core wire part.

30. The sensor guide wire according to claim 1, wherein an outer cross-sectional thickness of the proximal portion of the tip region core wire part is larger than an outer cross-sectional thickness of the intermediate portion of the tip region core wire part.

31. The sensor guide wire according to claim 1:
wherein the proximal region of the intermediate portion extends along approximately a proximal half of the intermediate portion and the distal region of the intermediate portion extends along approximately a distal half of the intermediate portion.

32. A sensor guide wire according to claim 1, wherein the proximal portion includes a non-tapered proximal region, and a tapered distal region that extends from a distal end of the non-tapered proximal region to a proximal end of the proximal region of the intermediate portion.

33. A sensor guide wire according to claim 1, wherein the distal region of the intermediate portion is not tapered so as to have a cross-sectional thickness that decreases in the distal direction.

34. A sensor guide wire according to claim 1, wherein the distal region of the intermediate portion is cylindrical.

* * * * *